(12) United States Patent
Shedd et al.

(10) Patent No.: US 8,574,603 B2
(45) Date of Patent: Nov. 5, 2013

(54) HATCHING KIT FOR TOXICITY TEST

(75) Inventors: Tommy R Shedd, Middletown, MD (US); Mark W Widder, Chambersburg, PA (US); Eugene Hull, New York, NY (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 801 days.

(21) Appl. No.: 11/340,757

(22) Filed: Jan. 27, 2006

(65) Prior Publication Data
US 2006/0140862 A1  Jun. 29, 2006

Related U.S. Application Data

(60) Division of application No. 10/454,821, filed on Jun. 5, 2003, now Pat. No. 7,094,417, which is a continuation of application No. 09/930,499, filed on Aug. 16, 2001, now abandoned.

(60) Provisional application No. 60/225,788, filed on Aug. 17, 2000.

(51) Int. Cl.
*A01N 25/00* (2006.01)
*A01K 63/02* (2006.01)
*A01K 61/00* (2006.01)

(52) U.S. Cl.
USPC ............. 424/405; 424/9.1; 424/9.2; 119/201; 119/215

(58) Field of Classification Search
None
See application file for complete search history.

(56) References Cited

U.S. PATENT DOCUMENTS 5,593,678 A * 1/1997 Evans et al. ................. 424/184.1

FOREIGN PATENT DOCUMENTS

WO  WO 02/13598 A2  2/2002

OTHER PUBLICATIONS

Hull, The Use of Diapausing Eggs fron Killfish for Rapid, Sensitive Biological Screening of Toxicants in the Aquatic Enviroment, 1995, 1-54.*
Abstract "Rapid Toxicity Sssessment Using the Annual Killfish *Nothobranchius Guentheri*", 15th Annual Meeting, Society of Enviornmental Toxicology and Chemistry, Ocober 30-Nov. 3, 1994.
Guidelines for Registering Pesticies in United States Enviornmental Protection Agency, Federal Registry, Pesticide Program, vol. 40, No. 123, Part II, Wednesday, Jun. 25, 1975, p. 26901-26912.
Shedd, Tommy R. et al., "Rapid Toxicity Assessment Using the Annnual Killifish *Nothobranchius guentheri*" Sith Symposium on Enviornmental Toxicology and Risk Assessment: Modelin and Risk Assessment, Apr. 1996.
Shedd, Tommy R. et al., "Evaluation of the Annual Killfish *Nothbranchius Guentheri* as a Tool for Rapid Acute Toxicity Screening", Enviornmental Toxicology and Chemistry, vol. 18, No. 10, Oct. 1999, pp. 2258-2261.
Toussaint, Margaret W. et al., "A Compraison of Standard Acute Toxicity Tests with Rapid-Screening Toxicity Test", Enviornmental Toxicology and Chemistry, vol. 14, No. 5, 1995, pp. 907-915.

* cited by examiner

*Primary Examiner* — Daniel Sullivan
*Assistant Examiner* — Kyle Purdy
(74) *Attorney, Agent, or Firm* — Elizabeth Arwine

(57) ABSTRACT

The invention is a method and kit for conducting a rapid toxicity test. Methods and kits according to the invention include an animal or plant species in diapause.

19 Claims, 1 Drawing Sheet

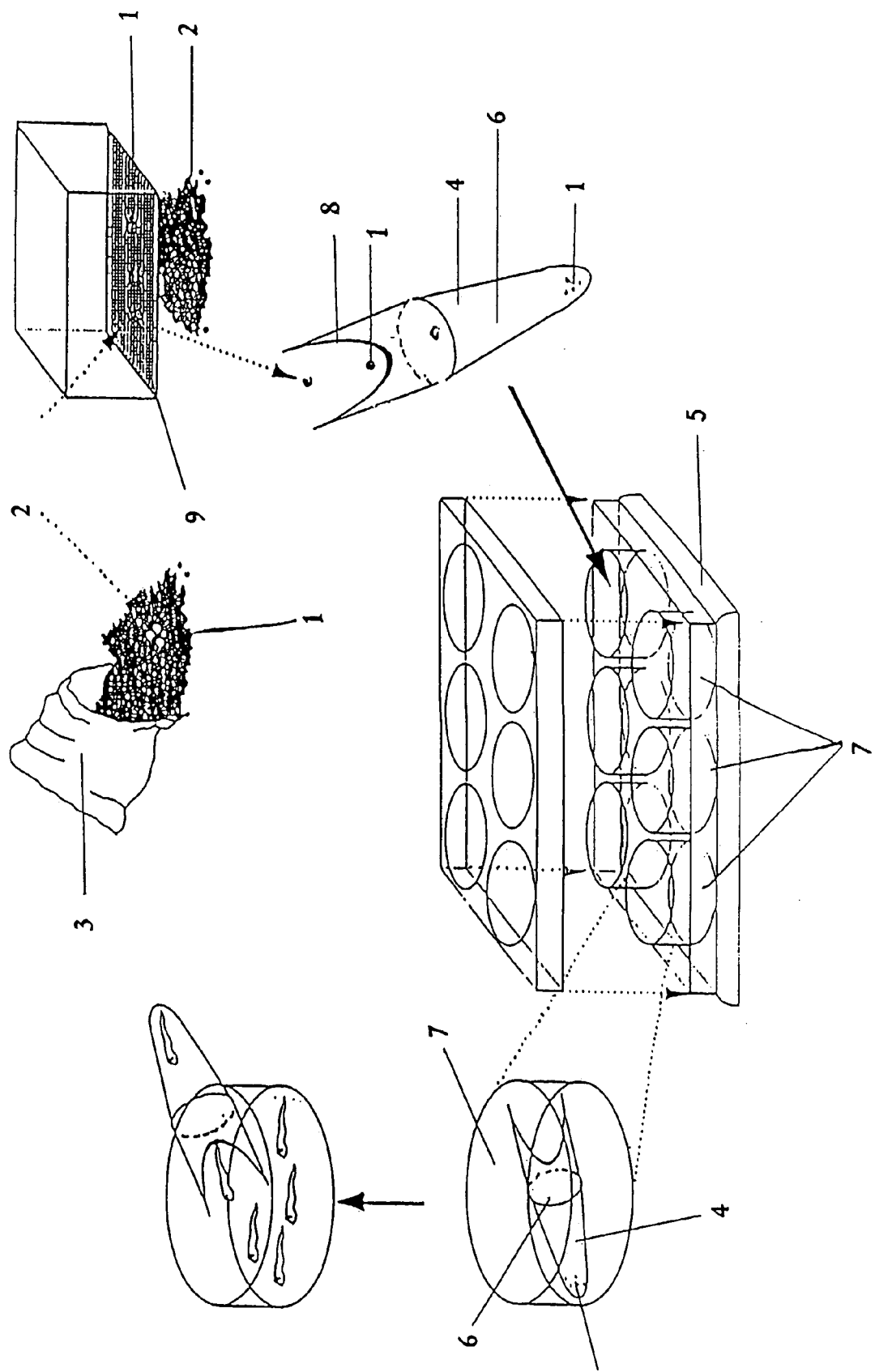

HATCHING KIT FOR TOXICITY TEST

CROSS-REFERENCE TO RELATED APPLICATIONS

This application is a divisional of U.S. patent application Ser. No. 10/454,821, filed Jun. 5, 2003, which is a continuation of U.S. patent application Ser. No. 09/930,499, filed Aug. 16, 2001, which claims the benefit of priority under 35 U.S.C. §119(e) of U.S. provisional Application Ser. No. 60/225,788, filed Aug. 17, 2001, all of which are hereby incorporated by reference.

STATEMENT REGARDING FEDERALLY SPONSORED RESEARCH

Not Applicable

BACKGROUND OF THE INVENTION

1. Field of the Invention

This invention relates to the field of animal husbandry. In particular, a rapid hatching fish embryo kit and method for using same is disclosed. The invention can be used in any application where it is desirable to store and/or transport fish embryos that can be removed from the storage media and hatched, preferably within about 48 hours. For example, the present invention can be used to perform rapid toxicity assessments in the field where it would otherwise be difficult to culture the fish necessary to perform such tests. In general, the present invention can be used as a convenient means for distributing fish to investigators, aquaculturists, hobbyists, and the like.

2. Description of Related Art

Annual fish are unique in that they are common only in habitats subject to erratic climatic conditions and complete seasonal drying. As their habitats dry, all hatched fish die, and species survival is totally dependent on the adults' substrate deposition of drought-resistant eggs which are capable of entering successive stages of diapause (suspended development). These eggs remain in a state of diapause until hatching is triggered by the onset of rainfall.

The use of fish to evaluate acute toxicity in the aquatic environment is common practice. Most fish models used in standard acute toxicity testing require labor intensive culture up to the moment they are to be used in a toxicity test. Substantial amounts of time and resources are required for culturing and maintaining healthy fish, for monitoring and maintaining water quality, for monitoring and maintaining environmental conditions, and for monitoring and maintaining appropriate biological cycles. Further, existing fish models typically require critical timing, certain well developed space requirements, and specific age requirements.

Classically, the use of fish and aquatic macro-invertebrates in standard acute toxicity tests for environmental risk hazard assessments has been exceedingly labor intensive and costly because of the need to maintain continuous cultures of healthy test organisms. Consequently, as the need for more wide-spread monitoring of environmental waters and effluents for preliminary indications of toxicity became increasingly apparent, a number of alternative tests systems not requiring continuous maintenance of organisms or cultures have been developed. Termed rapid screening toxicity tests, these tests systems commonly measure bacterial bioluminescence or respiration (e.g., Microtox, Azur Environmental, Carlsbad, Calif., USA; Polytox, Bethlehem, Pa., USA) and mortality or growth of organisms after emergence from resting life stages (e.g., rotifer cysts, brine shrimp cysts, or lettuce seeds).

In total, the existing acute toxicity testing methods involving fish present problems in terms of cost, timeliness, intensive labor requirements, and. specific environmental monitoring and maintenance.

*Nothobranchius guentheri* is an annual killifish indigenous to the coastal lowlands of Tanzania and Kenya. The embryonic development of *N. guentheri* has been extensively studied and is known to proceed through three successive stages, designated as diapause 1, 2, and 3. In diapause 1, the embryo is typically characterized as an undifferentiated mass of cells. In diapause 2, the embryo is typically characterized as being partially developed and having undifferentiated cells. In diapause 3, the embryo is typically characterized as being fully developed and ready to hatch in the presence of water or at the onset of rainfall.

Of the many variables affecting embryonic development, temperature has been most amply documented, and it is concluded that fully developed embryos were most sensitive to extremes and that diapause 2 embryos were less sensitive than diapause 1 embryos. Seasonal variations, including but not limited to light, light cycle, moisture content, and embryo proximity were also found to be important. Other factors known to affect the onset and duration of diapause included exposure to light, oxygen tension, partial desiccation, and exposure to ammonia.

SUMMARY OF THE INVENTION

The unique nature of the reproductive cycle of the annual killifish allows the long-term storage of diapause embryos under semi-dry laboratory conditions. Thus, toxicity evaluations are possible using fish as a test organism without the need to maintain a continuous population.

A test method has been developed in part to exploit these unique features, using newly hatched killifish (*Nothobranchius guentheri*) for rapid acute toxicity screening. Embryo culturing methods have been established and a storage media has been developed to allow convenient recovery of embryos for testing from storage media. After recovery, the embryos may be hatched from storage for use in a toxicity test.

The rapid fish acute toxicity test according to the present invention uses the killifish *Nothobranchius guentheri*. Recent studies have demonstrated that killifish can be mass cultured to produce large numbers of embryos in a suspended state (diapause). The embryos in diapause can be stored for long periods of time in semi-dry laboratory conditions for future toxicity testing. By changing the killifish embryo holding conditions, the embryos will hatch and the fry can be grown and used for testing. A fish toxicity test system that requires no culture at the time of testing would be especially useful and cost effective. The rapid killifish test could be conducted at any time without concern for culture system requirements to provide fish for testing, nor would conducting toxicity testing be subject to the vagaries of seasonal growth patterns and the delayed time associated with producing suitable test subjects.

The processes of the present invention were compared to the alternative test systems (using five representative protocols) and to standard acute toxicity tests, all of which were briefly identified in the Background section. The results for Microtox, rotifer (*Branchionus calyiflorus*), and lettuce (*Lactuca sativa*) compared favorably in sensitivity and reproducibility with those of the standard tests and were of shorter duration and exceedingly cost-effective. Further, the present invention provides the first "instant" or rapid test system involving a higher organism.

The accompanying drawing shows illustrative embodiments of the invention from which these and other of the objectives, novel features and advantages will be readily apparent.

DESCRIPTION OF THE DRAWING

FIG. 1 is a flow chart illustrating a method and kit of an embodiment of the invention.

DETAILED DESCRIPTION OF THE INVENTION

The present invention is a rapid test for analyzing toxicity comprising exposing a diapause species to a hatching medium, allowing the diapause species to form hatchlings, and exposing the hatchlings to toxicity test materials. In a preferred embodiment of the invention, the diapause species is a fish species. In a more preferred embodiment of the invention, the fish is an annual fish species. In a most preferred embodiment of the invention, the diapause species is a killifish, even more preferably, from the species *Nothobranchius guentheri*. In some embodiments of the invention, the species is in diapause 3.

In some embodiments of the invention, exposing a diapause species to a hatching medium includes a hatching medium comprising at least one of the following: water, ground water; any form of water that is non-toxic to the species being tested; and any form of water containing one or more nutrients and/or minerals. Typical minerals include, but are not limited to, inorganic minerals or salts, such as calcium, potassium, andlor magnesium containing compounds. Typically this is sufficient for a rapid or short term toxicity test. One skilled in the art will recognize that longer term tests, e.g., those that involve growth or a longer life span of the test species, may require other ingredients suitable for maintenance and survival of the species. Some embodiments of the invention further involve obtaining a species in diapause 3.

The present invention is also a method for testing the toxicity of a test material comprising exposing a test sample to hatchlings from a species that includes a diapause state, and determining the effect of the test sample on the hatchlings. Some embodiments of the invention further involve obtaining a species in diapause 3.

The present invention is also a method for distributing a species comprising obtaining a species in its diapause state, storing the species in a storage medium, shipping the storage medium containing the species to a predetermined location, separating the species from the storage medium, and exposing the species to a hatching medium. Some embodiments of the invention further involve obtaining a species in diapause 3.

Some embodiments of the present invention also include a storage medium for a species in its diapause state. A storage medium, according to the present invention comprises a composition suitable for maintaining a diapause species in its diapause state.

A process in accordance with the invention also may include the hatching medium capable of inducing growth and proliferation of the diapause species. The term "hatching medium" is used to describe a medium, such as a nutrient medium, that favors rapid growth of the species.

The present invention may also include a hatching apparatus comprising a container having a closed end and an open end, said closed end being shaped to position embryos placed therein in close proximity. In a preferred embodiment of the invention, the shape of the closed end is conical. In some embodiments of the invention, the open end further comprises one or more arcuate notches or the like.

The present invention also includes a kit for conducting a toxicity test, comprising a composition comprising a species in its diapause state and a storage medium, one or more containers for hatching the species, and one or more containers for exposing the hatchlings to a test material. The kit may also include one or more of the following: a container for storing the composition; a filter or the like for separating the species from the storage medium; a hatching medium; one or more growth factors or promoters suitable for adding to the hatching medium; one or more containers for culturing and/or growing hatchlings. Some embodiments of the invention further involve obtaining a species in diapause 3.

The present invention also includes a kit for conducting a toxicity test in accordance with the present invention, in combination with the devices and ingredients of other toxicity tests.

As used herein, diapause species refers to any living organism or cell having a diapause state. Exemplary diapause species include, but are not limited to, certain fish, chickens, almost all insects, and frogs. The diapause species may be an animal, plant, or microorganism species. Diapause state refers to a condition of suspended development or any pause occurring in the process of embryonic development. A diapause state may be induced or may be in response to an environmental condition. An example of inducing a diapause state may include mediating the diapause state using one or more diapause factors. One or more diapause factors may be included in or added to the solution containing the diapause species, and the factors may up-regulate or down-regulate the biological processes associated with entering diapause, maintaining diapause, and/or transitioning out of diapause.

An example of a response to an environmental condition may include a response to a drought condition, in which some fish species produce drought-resistant eggs that are capable of entering diapause, and remain in diapause until a sufficient amount of water or rain contacts the eggs. In a preferred embodiment of the invention, the diapause species is a fish species. In a more preferred embodiment of the invention, the fish is an annual fish species. In a most preferred embodiment of the invention,. the diapause species is a killifish, even more preferably, from the species *Nothobranchius guentheri*. Some embodiments of the invention further involve obtaining and/or using a species in diapause 3.

As used herein, storage medium refers to any medium or composition suitable for storing and maintaining a species in its diapause state. In a preferred embodiment of the invention, the storage medium maintains or controls the moisture content in a predetermined range suitable for the diapause species, and keeps individual embryos separated. A storage medium may be selected according to one or more of the following qualities: even insulative properties, maintaining a relatively constant humidity, ease of separation from the diapause species, non-toxic to the diapause species, and maintaining separation between individual embryos. Typical compositions may include at least one of the following: peat moss, refined peat moss, filter paper, processed paper and/or paper products. Water may also be used as a storage medium, but a container or structures to maintain separation between individual embryos should be used to maintain the embryos in diapause. Filter paper is preferred for short term storage; refined peat moss is preferred for long term storage, in part due to the ease of maintaining environmental conditions conducive to diapause embryo survivability.

In a preferred embodiment of the invention, the storage medium has a water content above about 50% by weight, preferably above about 75% by weight, up to about 100% by weight. Although the invention should not be restricted thereby, it has been found that maintaining the diapause embryos in their storage medium at greater than about 90% humidity is effective in producing a high proportion of hatchlings from the stored embryos.

The most preferred storage medium is refined peat moss, due in part to the ease of maintaining environmental conditions conducive to diapause embryo survivability, and the ease with which the diapause embryos may be separated from the medium when ready for use. As noted in more detail below and in the examples, peat moss may be refined by processing or filtering the peat moss to achieve a uniform particle size, typically less than about 0.6 mm (or a size that is smaller than the typical embryo size).

As used herein, hatching medium or hatching refers to any medium or composition suitable for inducing a diapause species to transition out of its diapause state. Typically, the hatching medium will stimulate embryo growth.

Finding the proper medium for inducing growth and/or a change of state is sometimes very difficult, with the cells of different species requiring diverse nutritional requirements. One skilled in the art will recognize that a particular species may require or benefit from a specific ingredient in the composition.

Typical hatching media in accordance with the invention may include water alone, or water including a carbon source, a source of inorganic ammonia (or ammonium ion), a source of phosphate, one or more hormones or animal/plant growth regulators, and optionally, other nutrient sources. Specific examples of hatching media in accordance with the invention are described in more detail below. Exemplary hatching medium includes but is not limited to water, deionized water, any form of water containing one or more growth factors or growth inducers.

Optionally, the storage medium and/or the hatching medium may include one or more salts to sufficient to reduce or eliminate fungal growth.

In a preferred embodiment of the invention, the hatching medium is deionized water. One skilled in the art will readily recognize that the content and other attributes of the water may be altered for a specific species or to achieve a specific result. Any additive to the medium that promotes and/or enhances survivability of the species may be used in the hatching medium. These alternative compositions are included in the present invention.

One skilled in the art will recognize that some water or medium parameters are well known as desirable attributes to hatch a species such as fish. Typically, the pH of the water is from about 6 to about 8; alkalinity of the water is typically from about 15 to about 35 mg/L (measured as $CaCO_3$), and the hardness of the water is typically from about 30 to about 50 mg/L (measured as $CaCO_3$).

As shown in the examples, water having a pH from about 7.75 to about 7.82, alkalinity from about 20 to about 28 mg/L (measured as $CaCO_3$), and hardness from about 40 to about 44 mg/L (measured as $CaCO_3$) has been found suitable for growth of *Nothobranchius guentheri*.

One skilled in the art will recognize that the hatching stage may occur under other various conditions. Conditions such as pH, temperature, light, and time may vary for different species in order to optimize cell growth. Further, it may be desirable to replace used hatching media with fresh hatching media since enzymes produced as a function of the hatching process may be toxic. For example, it may be desirable to transfer hatchlings from a hatching tube to a hatching dish, or similar larger container, in order to minimize or eliminate the effect of these enzymes.

It is understood that modifications may be made in the media such that substitution of other conventional salt compositions (such as organics, vitamins, amino acids, precursors, activators and inhibitors), addition or deletion of various components, growth regulators or alteration of proportions.

As used herein, the desirability of having embryos in close proximity as a precursor to hatching has been noted. Various phrases used herein to describe this concept refer to a natural phenomenon, the characteristics of which have not yet been fully elucidated. What is known is that a group of embryos touching each other typically hatch quickly, and that individual embryos fully separated from other embryos rarely or never hatch. In accordance with the present invention, hatching may include one or more steps or structures that promote or facilitate embryo contact or proximate positioning sufficient to induce or promote hatching.

As used herein, toxicity test refers to any test in which a species is contacted with a composition and evaluated for any deleterious effects from an ingredient in the composition. In a preferred embodiment of the invention, the hatching medium and the test medium are the same or include the same ingredients, except that the test medium further includes the one or more potentially toxic elements being tested. Diagnostic microbiology and toxicology typically base diagnoses on a macroscopic and/or microscopic examination of a living organism. The accuracy of the diagnosis and the preparation of optimally interpretable specimens typically depends upon adequate sample preparation, i.e., the rapidity with which a potentially toxic test sample.can be placed in contact with a test organism. A rapid toxicity test is defined in this application as a test that is 96 hours or less in duration, uses standard laboratory equipment, and has no continuous culture requirements to provide test organisms. Typical rapid toxicity tests are for about 24 hours or about 48 hours in duration. An exemplary time frame for *Nothobranchius guentheri* includes about 1 to 2 hours for initial hatching, about 24 hours for optimum hatching, and about 24 hours for exposure to a test composition containing one or more toxins.

The killifish test can be used in combination with other rapid tests to give a multi-tropic-level assessment at sensitivity levels near the standard EPA tests. Savings in culture and testing resources can be applied for a more complete contaminant or on-site screening evaluation to assess potential toxic impact on the environment. Other exemplary tests include, but are not limited to those described by the U.S. Environmental Protection Agency and acceptable toxicity tests. For example, the EPA has published "Methods of Measuring the Acute Toxicity of Effluents and Receiving Waters to Freshwater and Marine Organisms" (fourth edition), EPA/600/4-90/027 (September 1991), incorporated herein by reference.

The methods and kits of the present invention provide beneficial superiority over existing toxicity methods because: 1) embryos in diapause can be stored for an extended period at normal room temperature (about 21° to about 25° C.) before use; 2) hatching occurs rapidly, typically within about one to two hours after the embryos are placed in water; 3) the storage media maintains embryos in a desired diapause state and simplifies subsequent embryo separation from the storage media; 4) the size and shape of the hatching tubes encourage hatching to occur and reduce handling stress that could harm embryos and hatchlings; and 5) the culturing wells further reduce handling stress.

Referring to FIG. 1, illustrative concepts of the present invention are shown. By way of example, the invention is described in relation to the use of *Nothobranchius guentheri* as the diapause species. The invention as illustrated includes embryos 1, storage media 2, container 3, hatching tubes 4, culture plate 5, and culture water 6. During storage, container 3 holds embryos 1 and storage media 2, typically at normal room temperature (e.g., about 21° to about 25° C.). The diapause embryos can be maintained in this condition for up to about three years or more, any period within 0 to 3 years, and typically nine months or more before use, preferably between about 6 months and about 9 months. One skilled in the art will recognize that storing the diapause embryos in a vacuum pack or on a shaker may extend the storage period. One skilled in the art will also recognize that the embryos for some species may be stored for longer than nine months, but the chances for embryo degradation appear to increase over time.

When a toxicity test needs to be performed or the diapause species is ready for transition out of diapause, embryos 1 may be removed from container 3, separated from storage media 2, and placed into hatching tubes 4 with about 1 mL of the culture water 6. It has been found that the choice of the size and shape of the hatching tube, the amount of culture water, and the number of embryos in each hatching tube should be coordinated to promote contact among the embryos. This is based on the finding that separated embryos rarely hatch, but that embryos in close proximity to each other hatch, sometimes quickly.

The hatching tubes may then be placed into holding or growth cells 7. In a preferred embodiment of the invention, the hatching tube is placed in the holding cell 7 so that hatchlings can swim out of the hatching tube into the holding cell, but embryos are retained in the hatching tube. An exemplary configuration is shown in FIG. 1. In a most preferred embodiment of the invention, hatching tube 4 is set at an angle in holding cell 7. Further, the ability of the hatchling to remove itself from the hatching tube may be enhanced by providing a hatchling tube with one or more arcuate cut-outs 8.

After the first embryo hatches, approximately 10 mL of culture water 6 may then be added to each hatching tube to allow the hatchlings to swim free of hatching tubes 4 into the larger volume of holding cells 7.

In the preferred embodiment, embryos 1 are obtained from an annual fish species, preferably a killifish. In a preferred embodiment of the invention, the killifish is *Nothobranchius guentheri*, which is native to the coastal lowlands of Tanzania and Kenya. Annual fish are unique in that they are common only in habitats which are subject to complete seasonal drying and erratic climatic conditions.

The annual fish can be mass cultured to produce large numbers of embryos in diapause, according to a variety of methods known to those skilled in the art. Diapause embryos may be found in nature, or may be purchased from Orbis Scientific or Triops, Inc., both companies having a place of business in Pensacola, Fla.

Once the embryos are in diapause, they may be stored in a storage medium as noted above. One exemplary storage medium is refined peat moss, peat moss that ground to a particulate rating that will pass through a 0.6 mm sieve. As further illustrated below, grinding the peat sized to a predetermined particulate rating aids in the separation of embryos from storage media when the user is ready to begin culturing.

As noted above, in a preferred embodiment of then invention, the storage media is semi-dry. As used herein, semi-dry refers to the moisture content of the storage medium. In preferred embodiments of the invention, the storage medium should sufficiently moist to preserve the embryos. Without intending to be limited to a specific moisture content, the inventors have found that a moisture content between about 50% and about 80% by weight, preferably about 75% percent water by weight, is suitable for preserving *N. guentheri* embryos.

Preferred storage media are those that promote even insulative properties, maintain a constant humidity, allow ease of embryo removal, and is non-toxic to the embryos. For example, the storage media is preferably sterilized before use, e.g., by boiling or autoclaving. The peat moss or other media may be liquified and blended to reduce particulate size. Further, the media may be strained or filtered though sieve 9 or the like, e.g., a fine polypropylene mesh (typically, about 0.6 mm), to remove particles that exceed minimum embryo size. The storage media particulate size should be smaller than the embryos so that the embryos may be separated from the media by straining though the same mesh. After the media has been refined by blending and sifting, excess water may be removed by filtering the media though a brine shrimp net. The net may be lightly squeezed so that the media is not saturated with water but is still moist.

In the alternative, other compositions may be used as storage media, e.g., filter paper. Choice of storage media may be selected in part according to desired survival rates, as is well known to those skilled in the art.

Container 3 is preferably a sealable plastic bag, petri dish, or similar container for holding embryos 1 and storage media 2 during storage and/or transport. By using an inert and watertight container, embryos 1 may be protected from outside sources of contamination, and the moisture content of storage media 2 may be maintained or controlled.

Hatching tube 4 is generally conical in shape with beveled edges 10-11 and an approximate volume of 1 cc. The size and shape of hatching tube 4 causes the embryos to cluster near the bottom of the tube such that each embryo is generally in contact with two or more other embryos. In combination with the use of a hatching medium according to the invention, contact with other embryos appears to provide beneficial results, including but not limited to stimulating embryo growth.

Hatching generally occurs within 1 to 2 hours of embryo placement in the hatching tubes. When the hatching tube 4 is placed in culture plate 5 and additional water is added, beveled edges 10-11 provide a path for hatchlings to swim free of the hatching tube and into the larger volume of the culture plate. This eliminates handling stress that may result from the use of conventional transfer devices, e.g., a pipette or similar device.

Culture plate 5 is a multi-cell test culture plate.

Culture water 6 is a soft water suitable for hatching fish. In the preferred embodiment a deionized ASTM Type 1 water may be used. In the most preferred embodiments of the invention, the deionized water includes one or more inorganic salts, or one or more other ingredients used to reduce algae and/or fungal growth, including but not limited to $NaHCO_3$, $CaCl(2H_2O)$, $MgCl_2(6H_2O)$, $KCl$, and $NaCl$.

Typically the culture water and the test medium are the same, preferably both formulated according to conventional ASTM standards. Acceptable water quality parameters for the culture water 6 are: pH (7.75-7.82), alkalinity (20-28 mg/L as $CaCO_3$), hardness (40-44 mg/L as $CaCO_3$).

In a variety of industries, it may be desirable to determine the presence of a contaminant in a fluid such as air or water, e.g., contaminants in drinking water, or bacteria in food and beverage processing plants. In environmental analysis, it may be desirable to determine the presence, type, and amount of a certain contaminant, such as estrogenic compounds, pesticides (DDT, heptachlor, and atrazine), aromatic hydrocarbons, and polychlorinated biphenyls. In both the medical and environmental fields it may be desirable to determine the presence of breakdown products such as bisphenol-A, an ingredient in plastics.

The typical acute toxicity test will test for contaminants and the like in environmental effluent, will involve a dilution series of the effluent, and will test for toxicity as the endpoint of the analysis.

EXAMPLES

Example 1

Dilution Water Preparation. Dilution water utilized was a deionized ASTM Type 1 water with 48 mg/L $NaHCO_3$, 26 mg/L $CaCl(2H_2O)$, 51 mg/L $MgCl_2(6H_2O)$, 2 mg/L KCl, and 2 mg/L NaCl added. Acceptable water quality parameters for the dilution water were as follows: pH (7.75-7.82), alkalinity (20-28 mg/L as $CaCO_3$), hardness (40-44 mg/L as $CaCO_3$).

Embryo Storage And Receipt. Enough embryos were shipped via overnight airmail to perform tests (approximately 600 embryos per test chemical). Embryos received for testing were used immediately or placed in long-term storage at 21° C.-25° C. The storage area should be temperature controlled to avoid premature emergence of fry. The storage media consists of filter paper sealed in a petri dish (0 to 60 days) and/or a refined peat moss (particulate size <0.6 mm for greater than 60 days storage). Embryos were stored in these semi-humid conditions until needed for testing. The embryos were then extracted from the peat by straining the embryos through a 0.6 mm mesh.

Embryo Transfer. The embryos were rinsed from their storage media with dilution water into a petri dish. Temperature was maintained at 25° C. Dead, discolored, and prematurely hatched embryos were not used. Embryos were randomized using a disposable pipette into 24 separate hatching tubes containing 1 mL of dilution water.

Embryo Extraction And Hatching. Storage media containing embryos is saturated with culture water. The culture water should be in the range 20-25° C. Embryos were extracted from the storage media by pouring the liquified storage media through the 0.6 mm mesh. The embryos collected on the mesh were rinsed into a holding dish. Embryos were then transferred from the holding dish into the hatching tubes using a pipette. To achieve a pre-determined number of hatchlings in each cell well, 50% mortality was assumed, so two times the number of embryos were placed in each cell.

The hatching tubes were then placed into the empty culture plate cell wells. When the first killifish emerged from its egg case, 10 mL of temperature compensated water was added to the cell well. It is important that a sufficient amount of water infiltrates into the hatching tube so that newly hatched fry can swim freely from the hatching tube into the cell well. The hatching tubes were removed from the cell wells when the desired number of healthy fry was obtained in each cell well.

Hatching tubes containing fry and embryos were transferred into their respective test chambers when hatch was initiated. All hatching tubes were removed from the test wells within two hours of hatch initiation. Unhatched embryos and egg cases were removed from the test well. Fry were examined under the dissecting microscope. Malformed fry were noted and discarded. Remaining fry were incubated at 25° C. without light for a 24 hour period.

Test Fry Selection. At 24 hours post hatch, fry were examined under a dissecting microscope and all dead or malformed fry were removed. Fry were thinned to 10 fry per test well with a plastic disposable pipette.

Example 2

Embryo shipping and storage. Diapause 3 embryos stored in saline-moistened filter paper were shipped overnight from Triops (Pensacola, Fla., USA) and were used within 24 h of arrival for testing unless noted otherwise. A minimum of 600 embryos per test chemical was used. For long-term storage, embryos were placed in sterile (autoclaved), moist (75% water by weight) peat moss ground to a particular size of <0.6 mm. Embryos stored in this medium in the dark at 21 to 25° C. have remained viable for at least 9 months.

Hatching. The following procedure was developed to promote hatching and to minimize trauma to hatchlings during subsequent testing procedures. Culture water was deionized American Society for Testing and Materials type I water containing 48 mg/L $NaHCO_3$, 26 mg/L $CaCl—2H_2O$, 51 mg/L $MgCl_2—6H_2O$, 2 mg/L KCl, and 2 mg/L NaCl; the culture was aerated 24 hours before use. Acceptable parameters were pH 7.75 to 7.82; alkalinity, 20 to 28 mg/L (as $CaCO_3$); and hardness, 40 to 44 mg/L (as $CaCO_3$). Hatching tubes were 1.5-mL disposable polypropylene Eppendorf conical microcentrifuge tubes modified by a bevel cut at the top (see FIG. 1). When fish were needed, the embryos, received in filter paper storage, were washed into the hatching tubes with 1 mL of culture water. Embryos in long-term storage were separated by sieving the peat moss through a 0.6-mm polypropylene mesh screen and were similarly washed from the screen into the hatching tubes. The tubes, each containing about 20 embryos, were placed at a 45° angle in test wells containing 10 mL of culture water. The design of the hatching tube, with conical bottom and beveled edges, allowed the embryos to cluster at the bottom and enabled the hatchlings (fry) to swim freely into the test chambers without the stress of transfer (see FIG. 1). Hatching began within 1 hour, and 2 hours later the hatching tubes and any unhatched embryos and egg cases were removed from the test wells. Hatch rates ranged from 85 to 95% with a mean of 89%. Twenty-four hours after hatch, fry were examined with a dissecting microscope, and any damaged or malformed fry were removed. The fry were thinned to 10 per test well for subsequent toxicity test.

Example 3

Design of Toxicity Screenings

Test comunds. The 11 chemicals previously used for comparison of standard acute toxicity tests with rapid screening alternative procedures were selected. Zinc, cadmium, and copper were analyzed by inductively coupled argon plasma spectrometry; phenol, 2,4,-dichlorophenoxyacetic acid (2,4,-D), pentachlorophenol, and 2,4,6-trinitrotoluene (TNT), by high pressure liquid chromatography; malathion and 1-octanol, by gas chromatography; and sodium dodecyl sulfate, by ion chromatography. Unionized ammonia was analyzed with an Orion EA 940 specific ion analyzer (Beverly, Mass., USA) using an Orion model 95-12 ammonia electrode.

Test procedures. Toxicity tests were performed in triplicate at five concentrations (0.5 dilution factor) with control, in the same test wells in which fry were hatched (FIG. 1), in a Labline Biotronette incubator (Melrose Pak, Ill., USA) at 25° C. Nine milliliters of culture water was removed from each well and replaced with 9 mL of the test chemical solution in culture water. The wells were sealed with parafilm covered.

Reference tests with zinc as the toxicant were run alongside every test chemical to measure the batch variability of the killifish fry throughout the study. Tests were terminated after 24 hours, and the number of healthy, stressed, and dead fry in each test well were recorded. Healthy fry moved rapidly through the water and had constant, rapid pectoral fin movement. Fry were considered stressed when they were sluggish, swam irregularly, laid on their sides, or had faint pectoral fin movement and blood circulation. Dead fry were white and motionless and had no detectable heartbeat. The 24 hour median lethal concentration (LC50; death) and median effective concentration (EC50; stress) endpoints for each test compound were calculated using the trimmed Spearman-Karber method unless noted otherwise.

The 24 hour LC50 and EC50 endpoints for the *N. guentheri* toxicity tests are summarized in Table 1. Also included are comparable endpoints for the same test compounds obtained from the literature for five of the commonly used U.S. Environmental Protection Agency (U.S. EPA) standard test organisms maintained in continuous culture: water fleas (*Daphnia magna* and *Ceriodaphnia dubia*; 48-h EC50), green algae (*Selenastrum capricornium*; 96-h EC50), fathead minnows (*Pimephales promelas*; 96-h LC50), and mysid shrimp (*Mysidopsis bahia*; 96-h LC50).

Although the response of the standard test organisms to an individual toxicant is variable to the extent that no one organism is adequate to assess the toxicity of all classes of compounds, in general the sensitivity of the killifish test was in a range comparable to that of the other test organisms. For copper and unionized ammonia, the killifish test equaled or exceeded the standard methods in sensitivity, and for 1-octanol, phenol, PCP, 2,4-D, TNT, and SDS, the killifish sensitivities were within a range similar to those of the U.S. EPA test organisms. Although *D. magna* is known to be exceedingly sensitive to malathion, the killifish endpoints for the malathion were comparable to those observed for *P. promelas* and *M. bahia*. For zinc and cadmium, the sensitivity of the killifish was somewhat lower than that of the standard test systems but not greatly different from that observed for *P. promelas*.

Reproducibility of the killifish toxicity test endpoint has been documented by a series of experiments with zinc as the toxicant; these experiments were run at the same times as the experiments with each of the other 10 test chemicals. The results, summarized in Table 2, showed no substantial differences in toxicological endpoints for the fry emergent from the 10 different batches of embryos. The embryos were hatched within 1 or 2 days. after arrival for the experiments with each test chemical, but a succession of trials with zinc as toxicant on fry emergent from embryos stored at 21 to 25° C. for 30, 60, and 90 days showed no substantial differences in response to the toxicant (Table 2).

Comparison of the LC50 and EC50 endpoints for zinc in Table 2 showed that the fiducial limits of the latter were consistently narrower, and this trend was also true for the other 10 toxicants. Consequently, EC50 is the preferred parameter for use of *N. guentheri* as a test organism.

Conclusions: Evaluation of *N. guentheri* hatchlings as organisms for acute toxicity assessments has shown them to be comparable in sensitivity and reproducibility to a number of commonly used standard aquatic species in response to 11 representative toxicants, including heavy metals, unionized ammonia, biocides, and other trace organics. A major advantage of this species is that there is no need to maintain a continuous culture to have organisms immediately available for testing. Moreover, diapause 3 embryos remain viable for up to 9 months in moist peat moss and can readily be transported for on-site assessments of pollution. Other advantages include rapidity and simplicity of the assay; EC50 and LC50 endpoints can be determined after 24 h, and only standard laboratory equipment is required. Application of the method would provide substantial savings in culture and testing resources and permit more extensive and effective on-site screening of ambient waters and wastewater effluents for potentially adverse environmental impacts.

TABLE 2

Reproducibility of median lethal (LC50) and effective concentration (EC50) endpoints with zinc as toxicant (mg/L) in *Nothobranchius guentheri*[a]

| Reference test | LC50 | EC50 |
|---|---|---|
| 1 (Cd) | 7.7 (6.2-9.6) | 6.0 (4.7-7.8) |
| 2 (Cu) | 9.1 (7.5-11.1) | 6.4 (4.9-8.4) |
| 3 (unionized $NH_3$) | 15.1 (13.6-16.8) | 8.0 (5.8-11.0)[b] |
| 4 (1-octanol) | 10.8 (8.4-13.7) | 7.8 (5.7-10.6) |
| 5 (phenol) | 13.7 (10.8-17.5) | 8.0 (5.8-14.4)[b] |
| 6 (PCP) | 14.1 (12.2-16.4) | 8.2 (6.0-11.2) |
| 7 (TNT)[c] | 10.2 (7.9-13.2) | 7.6 (6.7-8.6) |
| 8 (malathion) | 11.7 (9.0-15.2) | 6.8 (5.2-9.0) |
| 9 (2,4-D)[d] | 7.1 (5.2-9.9) | 6.0 (4.7-7.7) |
| 10 (SDS) | 9.0 (7.9-10.2) | 8.2 (6.7-10.2) |
| 11 (30-d storage) | 16.9 (12.5-22.8) | 8.0 (6.1-10.5) |
| 12 (60-d storage) | 9.8 (7.0-13.9)[b] | 7.5 (6.0-9.2) |
| 13 (90-d storage) | 9.0 (7.9-10.2) | 4.6 (4.0-5.3) |

[a]Trimmed Spearman-Karber method [14] was used unless noted otherwise. Fiducial limits are given in parentheses.
[b]Binomial method [20] was used.
[c]TNT = 2,4,6-trinitrotoluene.
[d]2,4-D = 2,4-dichlorophenoxyacetic acid.

Example 4

Comparison of Rapid Annual Killifish Test vs. Standard Fathead Minnow Test

| Test Substance (mg/L) | *N. guentheri*[a] | | *P. promelas*[b] |
|---|---|---|---|
| | 24-HR LC50 | 24-HR EC50 | 96-hr LC50 |
| ZINC | 8.6 (7.49-9.88) | 5.75 (4.91-6.73) | 2.65 [0.87-4.7, N = 4] |
| CADMIUM | 4.2 (3.66-4.82) | 0.73 (0.64-0.84) | 2.02 [0.08-6.0, N = 6] |
| COPPER | 0.039 (0.033-0045) | 0.033 (0.028-0.039) | 0.48 [0.25-2.1, N = 8] |
| 1-OCTANOL | 22.8 (20.28-25.62) | 11.5 (10.35-12.8) | 13.5 [12.6-14.4, N = 6] |
| PHENOL | 56.7 (45.04-71.42) | 44.6 (36.71-54.29) | 30.3 [24.9-34.3, N = 8] |
| PCP | 0.25 (0.22-0.27) | 0.17 (0.14-0.20) | 0.23 [0.02-0.32, N = 7] |
| AMMONIA | 1.15 (0.98-1.35) | 0.57 (0.53-0.62) | 1.59 [1.04-1.59, N = 3] |
| TNT | 6.33 (5.41-7.4) | 3.34[c] (2.80-3.89) | 3.1 [2.6-3.7, N = 3] |
| MALATHION | 6.94 (5.84-8.25) | 2.91 (2.61-3.24) | 11.8 [8.7-12.5, N = 4] |
| SDS | 39.5 (37.0-42.2) | 31.11[c] (26.82-36.74) | 8.0 [6.2-9.6, N = 4] |

[a]Trimmed Speramian-Karber method for LC50 and EC50 (Fiducial Limits shown in parenthesis)
[b]Data from Toussaint et al., 1995; values represent a mean LC50 (LC50 range and number of references given in brackets)
[c]Moving average for calculation of EC50 value EC50 and LC50 results of the killifish test were compared to the fathead minnow standard EPA test results. Several compounds having various modes of toxicity including heavy metals, biocides, narcotics and common effluent constituents were evaluated. Analysis of the data revealed the rapid killifish test to be similar in sensitivity to the standard EPA test. There are several advantages to the killifish test: a 24 hour exposure duration, utilization of standard laboratory equipment, and no requirements for continuous culture on order to have fish available for toxicity screening.

Conclusions: Killifish test was similar in sensitivity to standard fathead minnow test. Killifish EC50's were more sensitive indicators of toxicity than LC50's for all compounds tested. Embryo batch variability in response to zinc exposure was low. EC50's were less variable than LC50's. Long-term storage of embryos did not affect LC50 sensitivity. Overall control mortality was low, <10%.

Although the present invention has been described in terms of a particular preferred embodiments, it is not limited to those embodiments. Alternative embodiments, examples, and modifications which would still be encompassed by the invention may be made by those 0skilled in the art, particularly in light of the foregoing teachings.

The invention claimed is:

1. A kit for conducting a toxicity test, comprising:
a first container including a plurality of embryos of a species in a diapause III state and a storage medium that maintains said embryos in a diapause III state, controls moisture content, and keeps the individual embryos separated;
a plurality of second containers, each second container comprising 1) a first conical closed end configured for receiving a plurality of said embryos in a diapause III state and a hatching medium for allowing said embryos to hatch into hatchlings and 2) a second open end having a beveled edge for contacting with 3 material to be tested for toxicity, wherein said second container facilitates embryo contact to induce or promote hatching;
and a third container comprising a plurality of holding cells configured to hold the plurality of second containers at an angle such that the plurality of holding cells holds the plurality of second containers at a 45 degree angle, thereby allowing hatchlings to swim free from the plurality of second containers into the plurality of holding cells.

2. The kit of claim 1, wherein said species is an annual fish species.

3. The kit of claim 2, wherein said annual fish species is a killifish.

4. The kit of claim 2, wherein said species is *Northobranchius guentheri*.

5. The kit of claim 1, wherein said storage medium has a moisture content above about 50%.

6. The kit of claim 5, wherein said moisture content is between about 50% and 80%.

7. The kit of claim 6, wherein said moisture content is about 75%.

8. The kit of claim 1, wherein said storage medium includes a solid material selected from the group consisting of peat moss, refined peat moss, filter paper and processed paper.

9. The kit of claim 1, wherein said first container includes individual compartments, each compartment configured to keep an individual one of said species separated from others of said species stored in said first container.

10. The kit of claim 1, further comprising a filter mechanism for separating said species from said storage medium.

11. The kit of claim 1, wherein said hatching medium comprises water.

12. The kit of claim 11, wherein said hatching medium further comprises a carbon source.

13. The kit of claim 11, wherein said hatching medium further comprises an inorganic mineral or an inorganic salt.

14. The kit of claim 13, wherein said hatching medium includes a member selected from the group consisting of calcium, magnesium, potassium, and ammonium ion.

15. The kit of claim 1, wherein the first container comprises a sealed plastic bag.

16. The kit of claim 1, wherein said hatching medium comprises deionized water having a pH of 6 to 8 and an inorganic salt.

17. The kit of claim 1, wherein the second container comprises a plurality of conical tubes, each conical tube having a volume of 1 mL, thereby causing embryos to cluster near the bottom of the tube such that each embryo is in contact with two or more other embryos.

18. The kit of claim 17, wherein each conical tube holds about 20 embryos.

19. The kit of claim 11, wherein said hatching medium further comprises $NaHCO_3$, $CaCl(2H_2O)$, $MgCl_2(6H_2O)$, KCl, and NaCl.

* * * * *